United States Patent
Latour et al.

(10) Patent No.: US 11,950,814 B2
(45) Date of Patent: Apr. 9, 2024

(54) ORTHOPEDIC PLATE WITH LOCKING COMPRESSION SLOT

(71) Applicant: Extremity Medical, LLC, Parsippany, NJ (US)

(72) Inventors: Michael Latour, Ramsey, NJ (US); Raymond Penzimer, Morristown, NJ (US); Brian Straus, Dallas, TX (US); Timothy P. Charlton, Los Angeles, CA (US)

(73) Assignee: Extremity Medical, LLC, Parsippany, NJ (US)

( * ) Notice: Subject to any disclaimer, the term of this patent is extended or adjusted under 35 U.S.C. 154(b) by 0 days.

(21) Appl. No.: 18/092,936

(22) Filed: Jan. 4, 2023

(65) Prior Publication Data
US 2023/0210567 A1 Jul. 6, 2023

Related U.S. Application Data

(60) Provisional application No. 63/296,412, filed on Jan. 4, 2022.

(51) Int. Cl.
*A61B 17/80* (2006.01)
(52) U.S. Cl.
CPC ...... *A61B 17/8014* (2013.01); *A61B 17/8057* (2013.01)
(58) Field of Classification Search
CPC .................. A61B 17/8014; A61B 17/8057
See application file for complete search history.

(56) References Cited

U.S. PATENT DOCUMENTS

| | | |
|---|---|---|
| 4,622,959 A | 11/1986 | Marcus |
| 4,827,917 A | 5/1989 | Brumfield |
| 5,032,125 A | 7/1991 | Durham |
| 5,549,610 A | 8/1996 | Russell et al. |
| 5,779,705 A | 7/1998 | Matthews |
| 5,984,681 A | 11/1999 | Huang |

(Continued)

FOREIGN PATENT DOCUMENTS

| | | | | |
|---|---|---|---|---|
| CN | 2513533 Y | 10/2002 | | |
| DE | 102006000948 A1 * | 10/2006 | ......... | A61B 17/1728 |

(Continued)

OTHER PUBLICATIONS

International Search Report & Written Opinion, dated May 8, 2023, ISA/US, PCT/US23/10070.

(Continued)

*Primary Examiner* — Larry E Waggle, Jr.
(74) *Attorney, Agent, or Firm* — Kelley Drye & Warren LLP

(57) ABSTRACT

Assemblies and methods for fixation of bone or bone fragments using an orthopedic plate having a slot that causes the bone or bone fragments to compress as a screw is inserted into the slot and rotated therein. By anchoring the orthopedic plate to a first bone or bone fragment and rotating the screw into the second bone or bone fragment at an angle that may be up to approximately fifteen degrees from perpendicular to the top surface of the orthopedic plate, the screw head causes the orthopedic plate to traverse away from the first screw thereby causing the first bone or bone fragment to be drawn toward and/or compress with the second bone or bone fragment.

13 Claims, 11 Drawing Sheets

(56) References Cited

U.S. PATENT DOCUMENTS

| | | | |
|---|---|---|---|
| 6,106,528 A | 8/2000 | Durham et al. | |
| 6,270,499 B1 | 8/2001 | Leu et al. | |
| 6,517,541 B1 | 2/2003 | Sesic | |
| 6,579,293 B1 | 6/2003 | Chandran | |
| 6,629,976 B1 | 10/2003 | Gnos et al. | |
| 6,669,701 B2 * | 12/2003 | Steiner | A61B 17/8061 |
| | | | 606/291 |
| 8,100,953 B2 * | 1/2012 | White | A61B 17/80 |
| | | | 606/280 |
| 8,182,485 B1 | 5/2012 | Gonzalez-Hernandez | |
| 8,252,032 B2 | 8/2012 | White et al. | |
| 8,303,589 B2 | 11/2012 | Tyber et al. | |
| 8,361,075 B2 | 1/2013 | Gonzalez-Hernandez | |
| 8,574,234 B2 | 11/2013 | Gonzalez-Hernandez | |
| 8,574,270 B2 | 11/2013 | Hess et al. | |
| 8,668,693 B2 | 3/2014 | Bernstein | |
| 8,888,825 B2 * | 11/2014 | Batsch | A61B 17/8057 |
| | | | 606/291 |
| 9,005,255 B2 | 4/2015 | Lewis et al. | |
| 9,017,329 B2 | 4/2015 | Tyber et al. | |
| 9,044,282 B2 | 6/2015 | Tyber et al. | |
| 11,298,166 B2 | 4/2022 | Tyber et al. | |
| 2003/0187447 A1 | 10/2003 | Ferrante | |
| 2005/0165395 A1 | 7/2005 | Orbay | |
| 2006/0142763 A1 | 6/2006 | Munro et al. | |
| 2006/0206044 A1 | 9/2006 | Simon | |
| 2006/0264946 A1 | 11/2006 | Young | |
| 2007/0123876 A1 | 5/2007 | Czartoski et al. | |
| 2007/0225714 A1 | 9/2007 | Gradl | |
| 2008/0015587 A1 | 1/2008 | Munoz | |
| 2011/0137313 A1 | 6/2011 | Jensen et al. | |
| 2012/0083848 A1 | 4/2012 | Gonzalez-Hernandez | |
| 2012/0226322 A1 | 9/2012 | Gonzalez-Hernandez | |
| 2013/0116734 A1 | 5/2013 | Gonzalez-Hernandez | |
| 2015/0073486 A1 | 3/2015 | Marotta et al. | |
| 2018/0256218 A1 | 9/2018 | Steinlauf | |
| 2018/0310972 A1 * | 11/2018 | Anding | A61B 17/8605 |

FOREIGN PATENT DOCUMENTS

| | | | |
|---|---|---|---|
| DE | 102006000948 | * | 3/2023 |
| EP | 0315338 | | 2/1993 |
| FR | 2861576 A1 | | 5/2005 |
| WO | WO 2008/003433 | | 1/2008 |

OTHER PUBLICATIONS

Omega3 System Hansson Twin Hook Operative Technique, Omega3, Stryker Corporation, 2006.

Tibiotalocalcaneal Fusion Using the VersaNail Surgical Technique, DePuy Orthopaedics, Inc., Warsaw, Indiana, USA, 2002.

Patent Corporation Treaty Application PCT/US2018/26953 International Search Report and Written Opinion of the International Searching Authority dated Jul. 6, 2018.

* cited by examiner

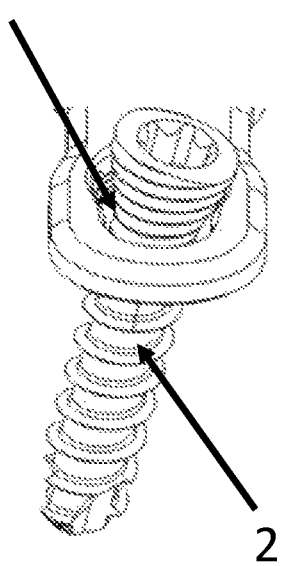
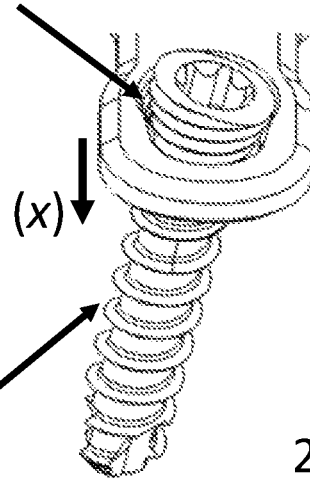
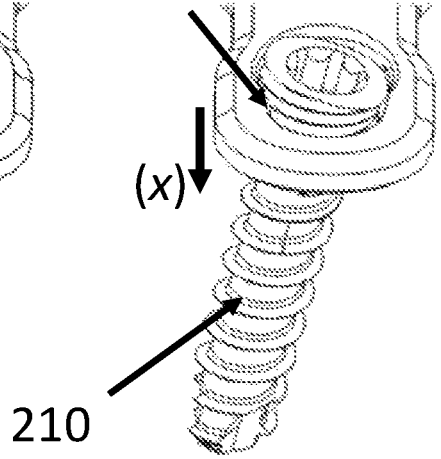
FIG. 6B  FIG. 6D  FIG. 6F
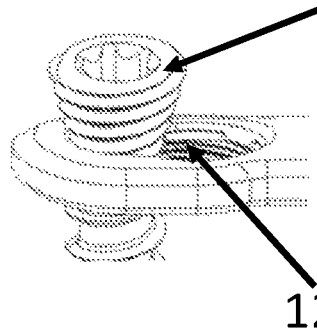
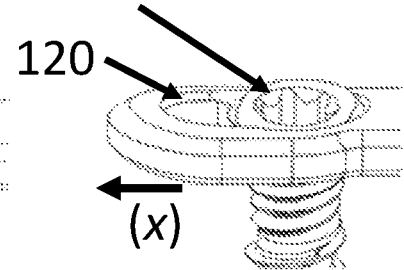
FIG. 6C  FIG. 6E  FIG. 6G

ORTHOPEDIC PLATE WITH LOCKING COMPRESSION SLOT

REFERENCE TO RELATED APPLICATIONS

This application claims the benefit of U.S. Provisional Patent Application No. 63/296,412, filed Jan. 4, 2022, the entire contents of which are incorporated herein by reference.

FIELD OF THE INVENTION

This invention relates to the field of implant devices for bone fixation, and more particularly, to an orthopedic plate having a slot configured to receive a screw, cause the orthopedic plate to traverse longitudinally along the axis of the slot as the screw advances into the slot, and cause the screw to lock in the slot.

BACKGROUND OF THE INVENTION

Orthopedic plates are typically used to join two bones together, for example two adjoining phalangeal bones of the foot. As used herein, the term "bone" refers to a bone, part of a bone, or a fragment of a bone.

Orthopedic plates typically have a plurality of apertures for receiving one or more screws or posts. The leading ends of the screws or posts may be inserted through one or more of the apertures and implanted into one of the bones. The plates and screws maintain the position and orientation of the bones and provide stabilization.

It may also be desirable to impart compression to bones by, for example, implanting an orthopedic plate and one or more compression screws. Certain bone plates capable of providing compression in addition to stabilization have been developed. For example, U.S. Pat. No. 9,005,255 discloses an orthopedic plate with a compression housing that receives a compression screw. However, the angle at which the compression screw may be implanted is limited to a specific angle determined by the shape of the compression housing. Also, U.S. Pat. Nos. 8,574,270 and 8,974,504 disclose bone plates having multiple segments, and springs that provide a contractive force to compress the segments together. However, the construction of such multi-segment bone plates is complex and expensive, and the amount of compressive force generated is limited to the tensile force of the springs.

SUMMARY OF THE INVENTION

The present invention is directed to improved assemblies for bone fixation.

It is an object of the present invention to provide an assembly comprising an orthopedic plate having a slot that, when a screw is inserted therein, causes the orthopedic plate to traverse relative to the screw and lock the screw in place to provide angular stability. The screw and slot may be configured to allow the screw to be inserted at an angle of between perpendicular and approximately 15 degrees from perpendicular to the top surface of the orthopedic plate.

Numerous variations may be practiced in the preferred embodiment.

BRIEF DESCRIPTION OF THE DRAWINGS

A further understanding of the invention can be obtained by reference to exemplary embodiments set forth in the illustrations of the accompanying drawings. Although the illustrated embodiments are merely exemplary of systems, methods, and apparatuses for carrying out the invention, both the organization and method of operation of the invention, in general, together with further objectives and advantages thereof, may be more easily understood by reference to the drawings and the following description. Like reference numbers generally refer to like features (e.g., functionally similar and/or structurally similar elements).

The drawings are not necessarily depicted to scale; in some instances, various aspects of the subject matter disclosed herein may be shown exaggerated or enlarged in the drawings to facilitate an understanding of different features. Also, the drawings are not intended to limit the scope of this invention, which is set forth with particularity in the claims as appended hereto or as subsequently amended, but merely to clarify and exemplify the invention.

FIGS. 6A-6G depict a screw inserted into a slot of an orthopedic plate in accordance with the present invention;

DETAILED DESCRIPTION OF THE INVENTION

Figure 1A:
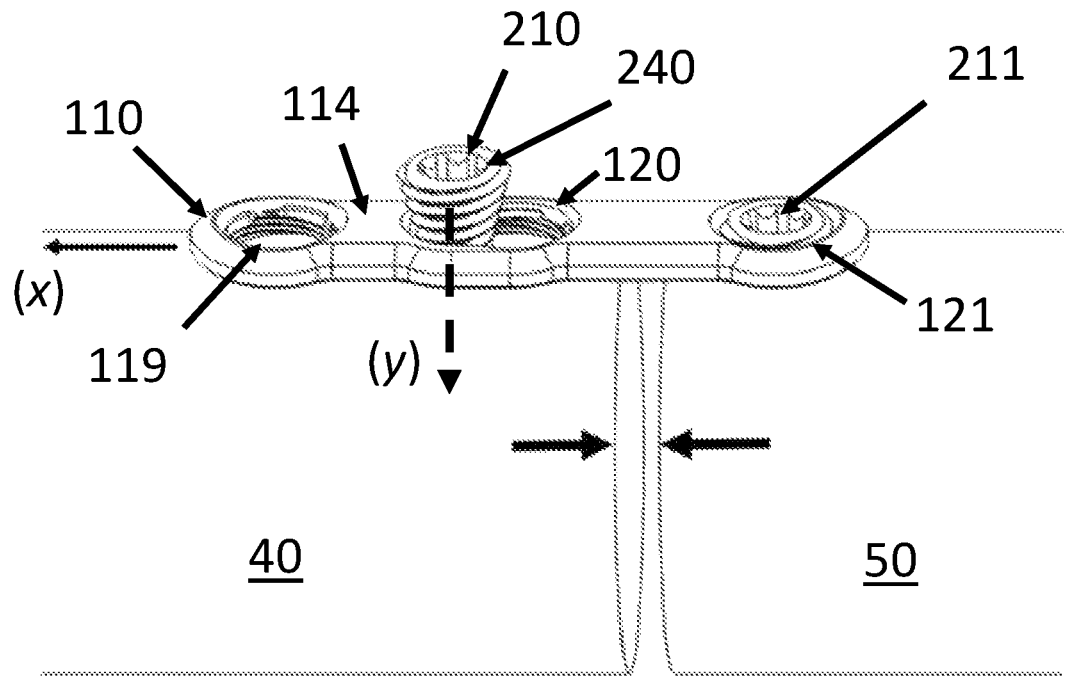
FIGS. 1A and 1B depict an assembly used to compress bones in accordance with the present invention.

The invention may be understood more readily by reference to the following detailed descriptions of embodiments of the invention. However, techniques, systems, and operating structures in accordance with the invention may be embodied in a wide variety of forms and modes, some of which may be quite different from those in the disclosed embodiments. Also, the features and elements disclosed herein may be combined to form various combinations without exclusivity, unless expressly stated otherwise. Consequently, the specific structural and functional details disclosed herein are merely representative. Yet, in that regard, they are deemed to afford the best embodiments for purposes of disclosure and to provide a basis for the claims herein, which define the scope of the invention. It should also be noted that, as used in the specification and the appended claims, the singular forms "a", "an", and "the" include plural referents unless the context clearly indicates otherwise.

Use of the term "exemplary" means illustrative or by way of example, and any reference herein to "the invention" is not intended to restrict or limit the invention to the exact features or steps of any one or more of the exemplary embodiments disclosed in the present specification. Also, repeated use of the phrase "in one embodiment," "in an exemplary embodiment," or similar phrases do not necessarily refer to the same embodiment, although they may. It is also noted that terms like "preferably," "commonly," and "typically," are not used herein to limit the scope of the claimed invention or to imply that certain features are critical, essential, or even important to the structure or function of the claimed invention. Rather, those terms are merely intended to highlight alternative or additional features that may or may not be used in a particular embodiment of the present invention.

For exemplary methods or processes of the invention, the sequence and/or arrangement of steps described herein are illustrative and not restrictive. Accordingly, it should be understood that, although steps of various processes or methods may be shown and described as being in a sequence or temporal arrangement, the steps of any such processes or methods are not limited to being carried out in any particular sequence or arrangement, absent an indication otherwise. Indeed, the steps in such processes or methods generally may be carried out in various different sequences and arrangements while still falling within the scope of the present invention.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Figure 1B:
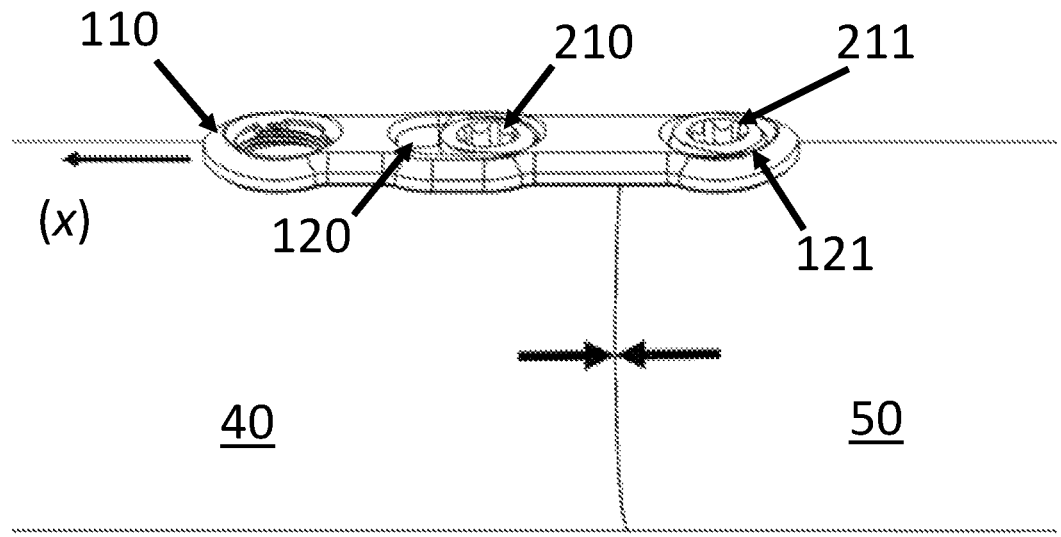

FIGS. 1A and 1B depict an orthopedic plate (110) in accordance with the present invention. Orthopedic plate (110) may be used to join, for example, a first bone (40) and a second bone (50). Orthopedic plate (110) may have a top surface (114) and a bottom surface (not shown), and may have one or more apertures (119, 120, 121). Orthopedic plate (110) may be aligned with first bone (40) and second bone (50) so that a first portion of the bottom surface of orthopedic plate (110) is adjacent to an outer surface of first bone (40), and a second portion of the bottom surface of orthopedic plate (110) is adjacent to an outer surface of second bone (50).

In accordance with the present invention, and as discussed further below, one or more apertures (119, 120, 121) in orthopedic plate (110) may be a slot having generally a "stadium" shape. A first screw (210) may have a head (240) and may be inserted in a first aperture (120) and into first bone (40), as discussed further below. A second screw (211) may be inserted in a second aperture (121) and into second bone (50). Second screw (211) may be configured to mate with aperture (121) by, for example, an interference fit or by complementary threads on second screw (211) and the interior surface of aperture (121). A portion of first screw (210) may be inserted into first aperture (120) before second screw (211) is inserted into second aperture (121), but preferably second screw (211) is fully inserted into second aperture (121) before head (240) of first screw (210) contacts first aperture (120). As discussed further below, as first screw (210) is inserted into aperture (120), head (240) of first screw (210) may engage a first angled ramp (152) and/or a second angled ramp (154), shown in FIG. 2A, along the interior surface of aperture (120), causing orthopedic plate (110) to traverse in a direction (x) orthogonally or substantially orthogonally to the direction (y) in which first screw (210) is advancing into first bone (40), thereby bringing first bone (40) and second bone (50) together and/or compressing first bone (40) and second bone (50).

Figure 1C:
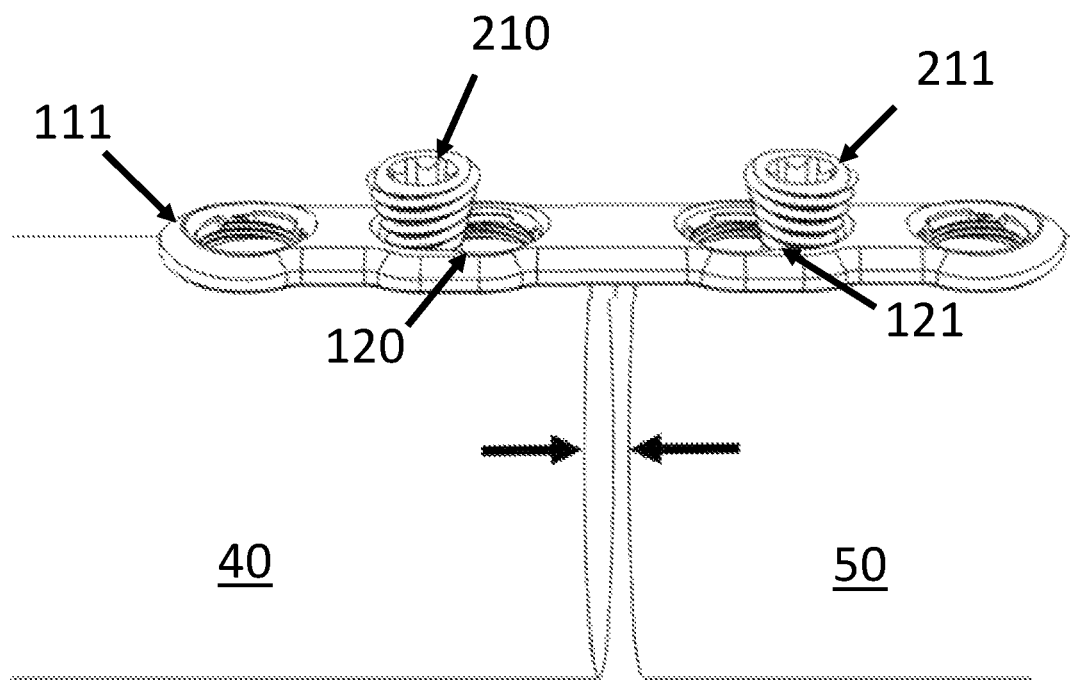
FIG. 1C depicts an alternate assembly in accordance with the present invention.

FIG. 1C depicts an alternate orthopedic plate (111) in which second aperture (121) is a slot that may be configured so as to match the description provided herein for aperture (120). Additionally or alternatively, second screw (211) may be configured so as to match the description provided herein for first screw (210). Preferably aperture (121) is oriented in orthopedic plate (111) so that as second screw (211) is inserted into aperture (121), it causes orthopedic plate (111) to traverse in a direction that is directly opposite to the direction (x) in which first screw (210) causes orthopedic plate (111) to traverse, which may bring first bone (40) and second bone (50) together and/or compressing first bone (40) and second bone (50).

Figure 2A:
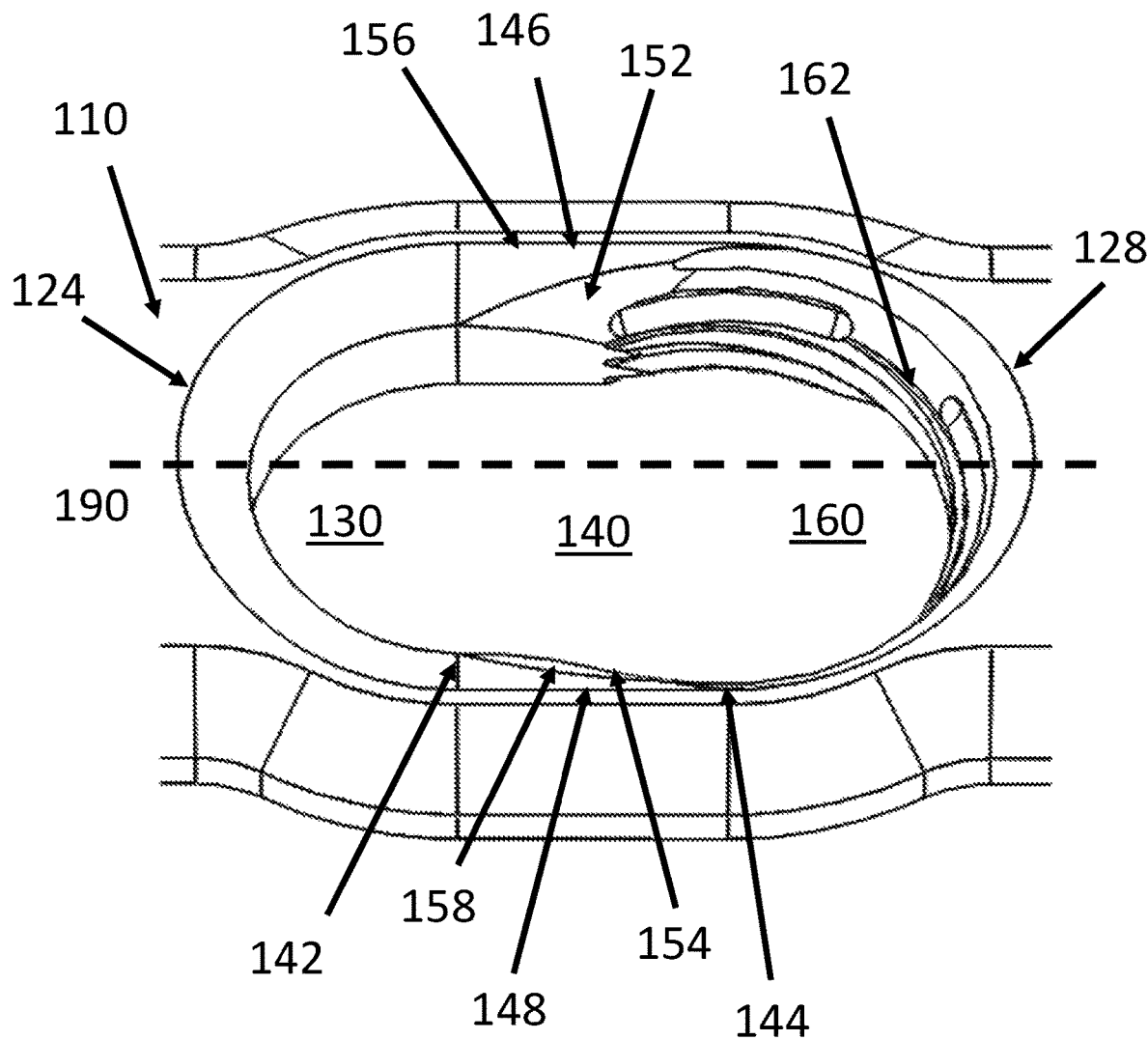
FIG. 2A depicts a slot in an orthopedic plate in accordance with the present invention.

As shown in FIG. 2A, first aperture (120) may be shaped as a slot extending along a longitudinal axis (190) from a first end (124) to a second end (128) and may have a "stadium" shape. First aperture may comprise three sections: a first semicircular portion (130), a second semicircular portion (160), and a middle section (140) between the first and semicircular portions (130, 160). The rectangular portion may extend lengthwise along a longitudinal axis (180) from a first end (142) to a second end (144).

Rectangular portion (140) may comprise a first side (146) and a second side (148). First side (146) may have an interior surface (156), and second side (148) may have an interior surface (158). One or both of interior surface (156) of first side (146) and interior surface (158) of second side (148) may comprise an angled ramp (152, 154). Each angled ramp (152, 154) may start at or near first end (142) of rectangular section (140). Alternatively, each angled ramp (152, 154) may start within the first semicircular portion (130). Additionally or alternatively, each angled ramp (152, 154) may extend into second semicircular portion (160).

Each angled ramp (152, 154) may be angled so that the end of the angled ramp (152, 154) closest to the first end of rectangular portion (140) is nearer to the top surface of orthopedic plate (110) than the opposite end of angled ramp (152, 154). The surface of each angled ramp (152, 154) may be flat or may be convex or concave. Each angled ramp (152, 154) may extend downward in the direction of second semicircular section (160). Each angled ramp may extend to or near second end (144) of rectangular portion (140).

First semicircular portion (130) may extend from first end (142) of rectangular portion (140), and second semicircular portion (160) may extend from second end (144) of rectangular portion (140). The diameter of first semicircular portion (130) and/or the diameter of second semicircular portion (160) may be the same or substantially the same as the width of rectangular portion (140). Preferably, first semicircular portion (130) and second semicircular portion (160) do not intersect. The top edge and/or bottom edge of first semicircular portion (130) and/or second semicircular portion (160) may be chamfered. Second semicircular portion (160) may have a threaded interior surface (162).

Figure 2B:
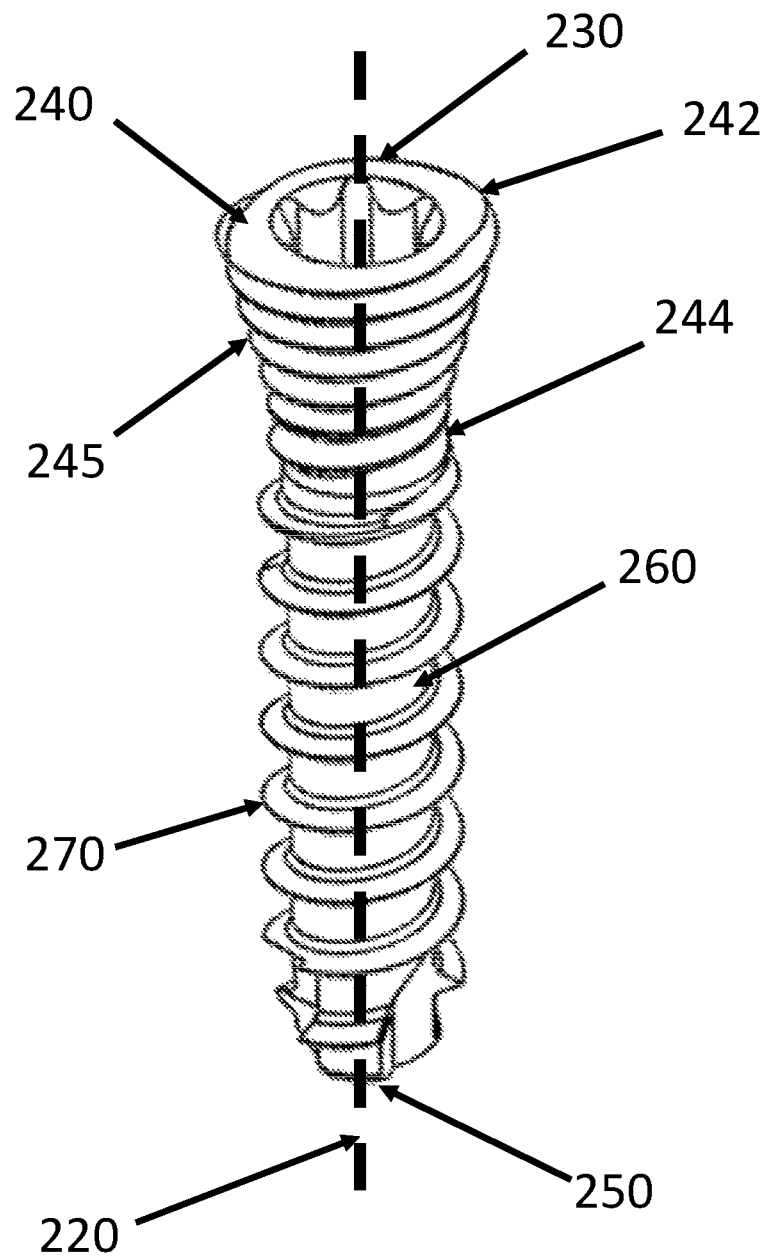
FIG. 2B depicts a screw configured to be inserted in the slot of an orthopedic plate in accordance with the present invention.

FIG. 2B depicts an exemplary first screw (210) configured to be inserted in aperture (120) of orthopedic plate (110). First screw (210) may extend along a first longitudinal axis (220) from a first end (230) to a second end (250). Screw (210) may comprise a head (240) at the first end (210) and a shaft (260) extending from head (240) to second end (250). Head (240) may extend from a top end (242) to a bottom end (244), and may have an outer surface comprising one or more threads (245). The one or more threads (245) may extend from top end (242) to bottom end (244). Alternatively, the one or more threads (245) may extend partially along the outer surface of head (240). As shown in FIG. 2B, head (240) of first screw (210) may, for example, have a truncated conical shape. The outer surface of head (240) may form an angle to the first longitudinal axis (220) that is approximately 15 degrees.

The outer surface of shaft (260) may also comprise one or more threads (270) that extend from the bottom end (244) of head (240) to second end (250) of first screw (210), or may extend along part of shaft (260). Alternatively or additionally, threads (245) on outer surface of head (240) may extend along shaft (260) for part or all of shaft (260). Second end (250) of screw (210) may comprise a self-tapping tip.

Figures 3A, 3B, 3C:
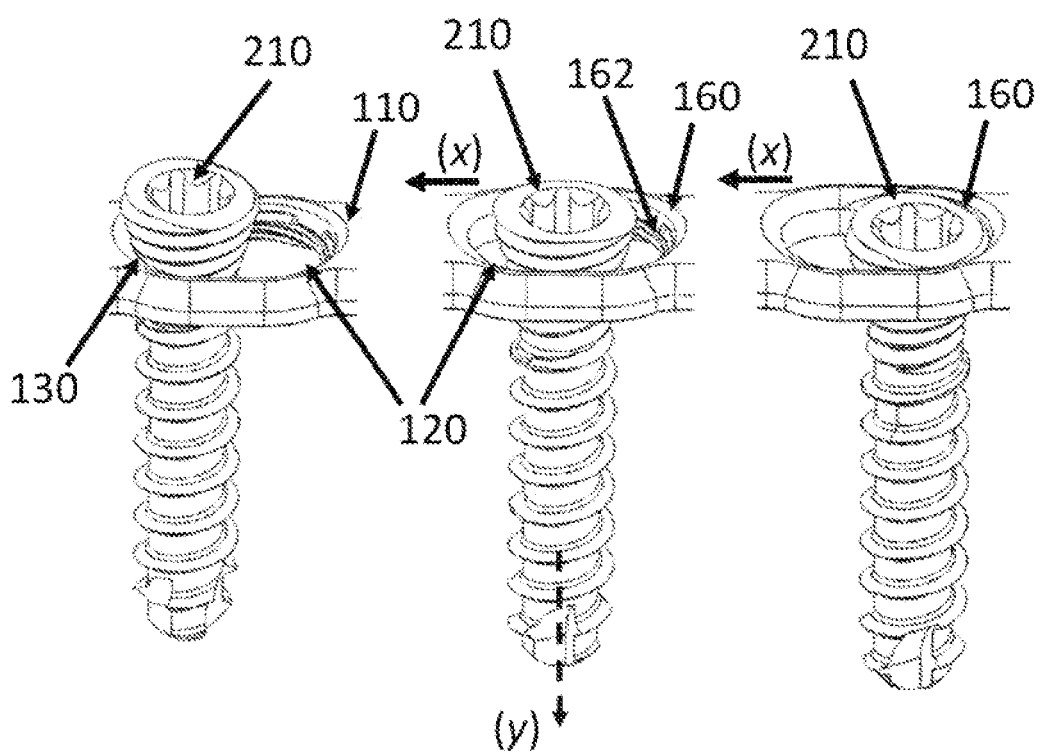
FIGS. 3A-3C depict a screw inserted into a slot of an orthopedic plate in accordance with the present invention.

Referring to FIGS. 3A-3C, a first screw (210) may be inserted in aperture (120) of orthopedic plate (110). As shown in FIG. 3A, first screw (210) may be inserted into first semicircular portion (130) of aperture (120) of orthopedic plate (110). Referring to FIG. 3B, as first screw is advanced into aperture (120), head (240) of first screw (210) may contact first angled ramp and/or second angled ramp (152, 154, not shown) along the interior surface of aperture (120). As screw (210) is advanced further into aperture (120), head (240) of first screw (210) may apply force to the first angled ramp and/or second angled ramp (152, 154) in the direction (y) in which screw (210) is advancing. The applied force may cause orthopedic plate (110) to traverse in a direction (x) orthogonal to or substantially orthogonal to direction (y) in which the screw is advancing into first bone (40).

Figure 4:
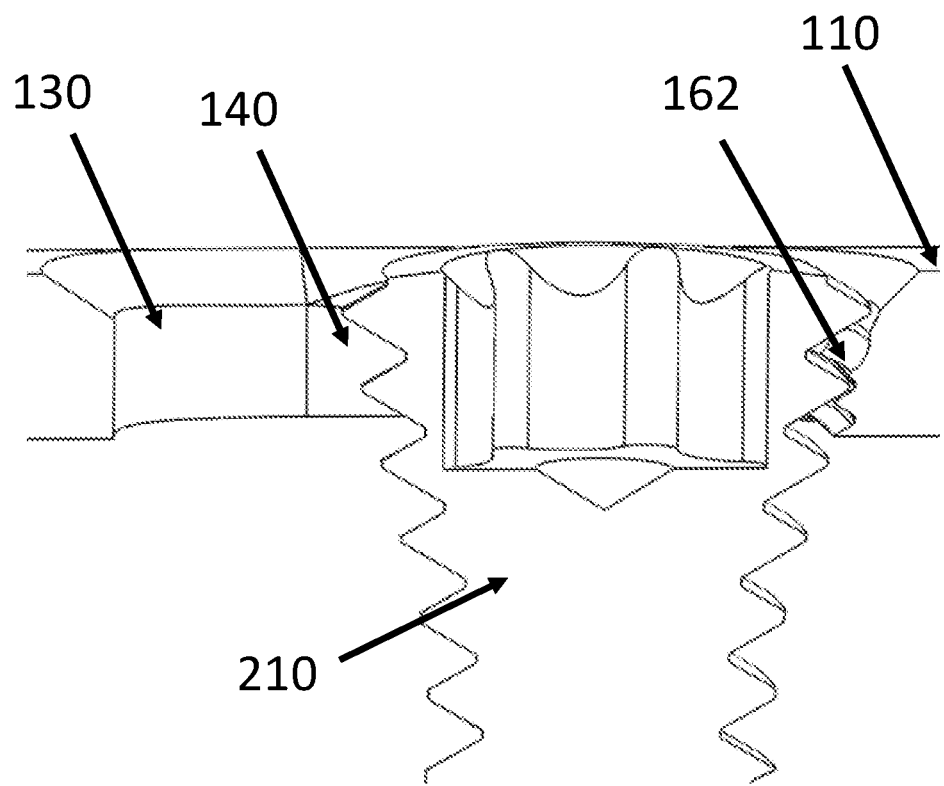
FIG. 4 depicts a cross-section of a screw head as inserted in a slot of an orthopedic plate in accordance with the present invention.

Referring to FIG. 3C, first screw (210) may be advanced into aperture (120) until head (240) of first screw (210) is inserted into second semicircular portion (160) of aperture (120). FIG. 4 depicts a cross-sectional view of head (240) inserted into second semicircular portion (160) of aperture (120). One or more threads (340) on head (240) of first screw (210) may be configured to mate with and/or lock to one or more threads (162) on the interior surface of second semicircular portion (160) of aperture (120). For example, threads (240) may lock to threads (162) as disclosed in U.S. Pat. No. 10,149,708, incorporated herein by reference.

As shown in FIGS. 5A-5E, in accordance with the present invention, first screw (210) may be inserted at an angle (a) into first aperture (120). For example, first screw (210) may be asserted at an angle (a) that is between zero and fifteen degrees from perpendicular to top surface (114) of orthopedic plate (110). As shown in FIGS. 5A-5E, angle (a) may extend in the same direction as longitudinal axis (190) of first aperture (120).

Figure 5A:
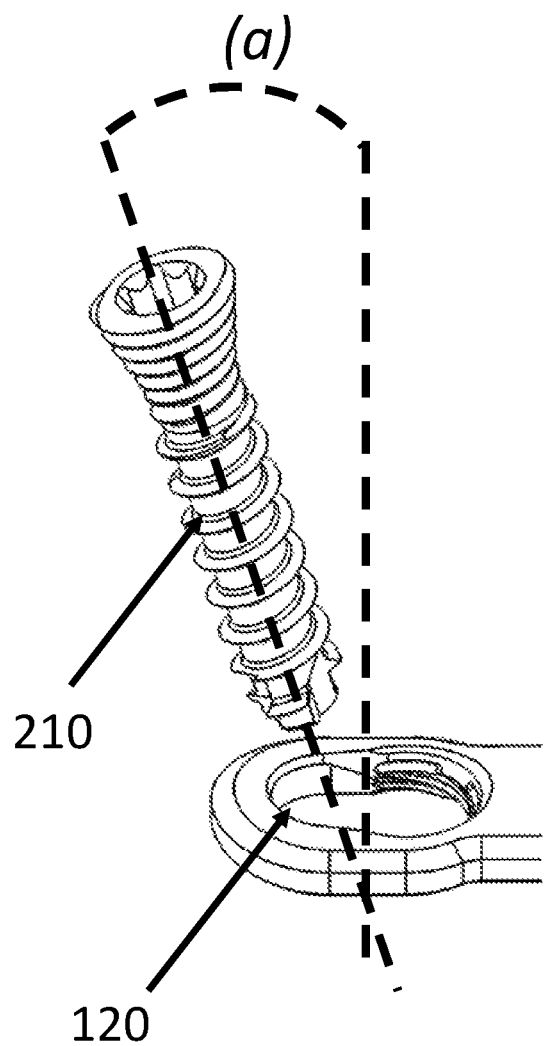
FIGS. 5A and 5B depict a screw inserted into a slot of an orthopedic plate in accordance with the present invention.
Figure 5B:
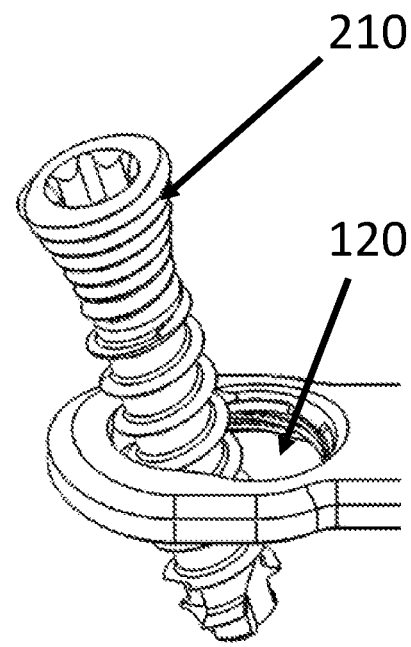
Figure 5C:
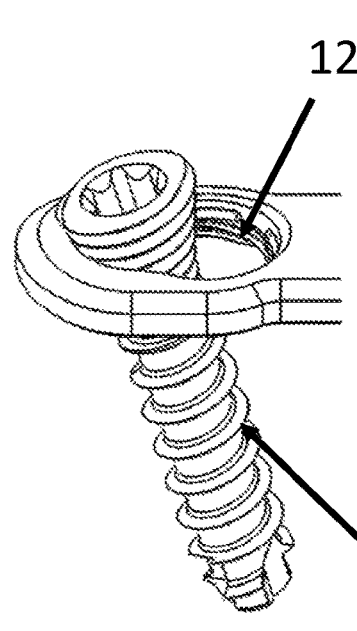
FIGS. 5C-5E depict the screw and orthopedic plate depicted in FIGS. 5A and 5B as the screw is further advance into the slot in the orthopedic plate.
Figure 5D:
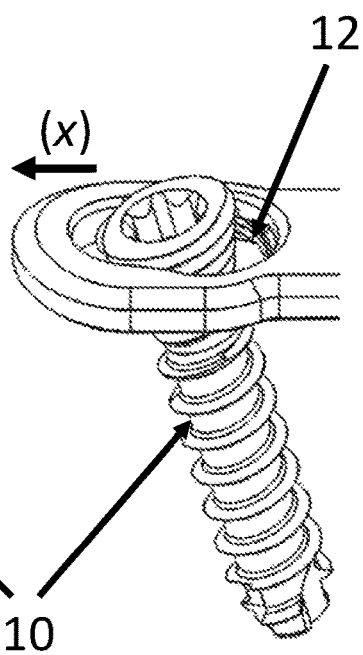
Figure 5E:
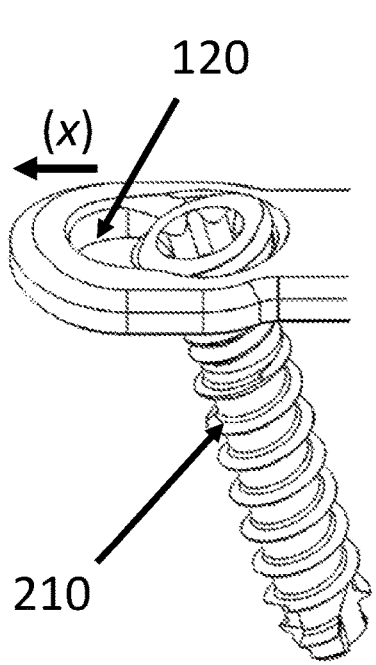

Referring to FIGS. 5B-5E, as first screw is advanced into aperture (120), head (240) of first screw (210) may contact first angled ramp (152) and/or second angled ramp (154, not shown), as shown in FIG. 5C. As shown in FIG. 5D, as screw (210) is advanced further into aperture (120) at angle (a), head (240) of first screw (210) may apply force to the first angled ramp (152) and/or second angled ramp (154), causing orthopedic plate (110) to traverse in a direction (x). First screw (210) may be advanced into aperture (120) until head (240) of first screw (210) is inserted into second semicircular portion (160) of aperture (120), as shown in FIG. 5E.

One or more threads (340) on head (240) of first screw (210) may be configured to mate with and/or lock to one or more threads (162) on the interior surface of second semicircular portion (160) of aperture (120). Additionally or alternatively, the one or more threads (340) on head (240) may be configured to cut into the interior surface of second semicircular portion (160) of aperture (120). The compression described above applied to, for example, first bone (40) and second bone (50), is held firmly in place when the head (240) of first screw (210) locks to threads (162) and/or interior surface of second semicircular portion (160) of aperture (120).

Figure 6A:
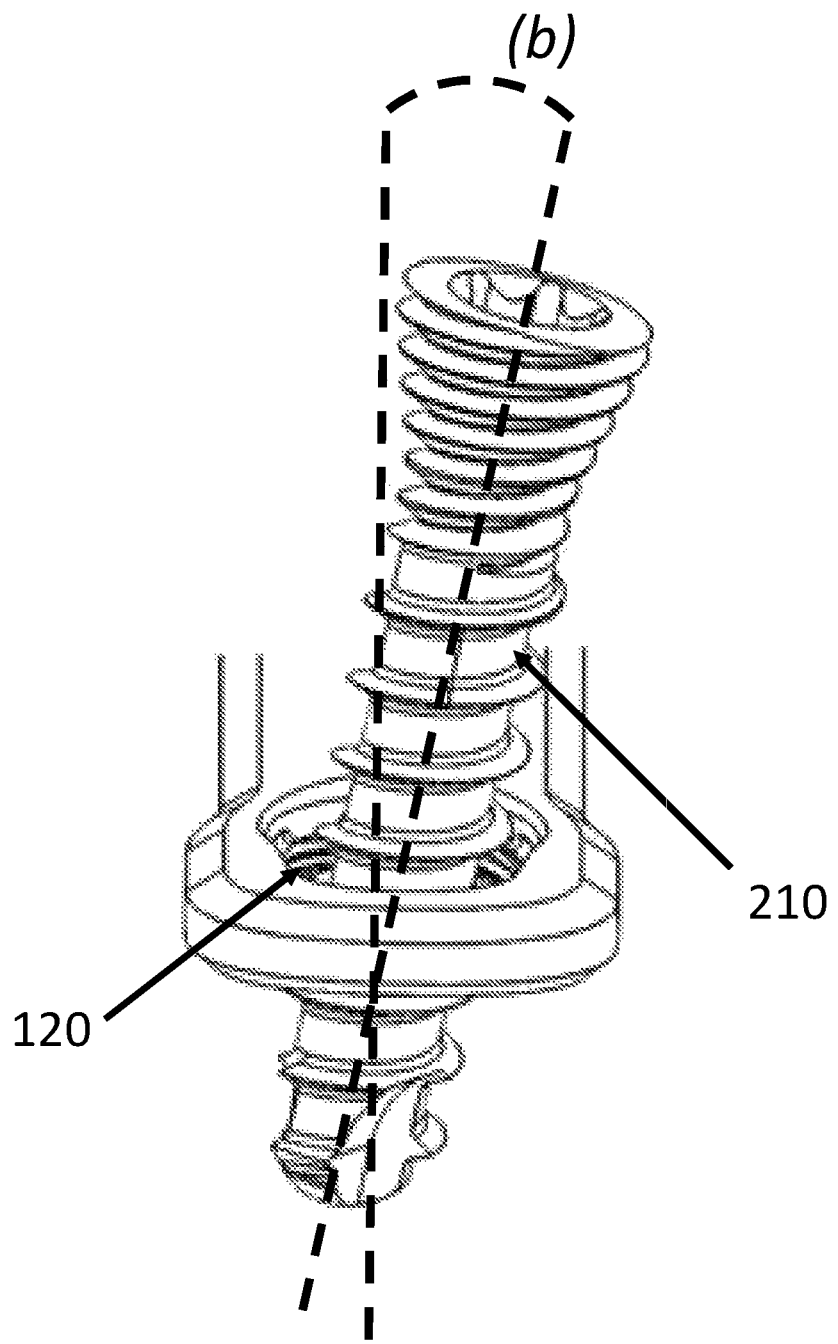

As shown in FIGS. 6A-6G, in accordance with the present invention, first screw (210) may be inserted at an angle (b) into first aperture (120). For example, first screw (210) may be asserted at an angle (b) that is between zero and fifteen degrees from perpendicular to top surface (114) of orthopedic plate (110), but in a direction that is not along longitudinal axis (190) of first aperture (120). For example, angle (b) may be orthogonal to longitudinal axis (190) of first aperture (120). Referring to FIGS. 6B-6G, as first screw is advanced into aperture (120), head (240) of first screw (210) may contact first angled ramp (152) and/or second angled ramp (154, not shown), as shown in FIGS. 6B and 6C. As shown in FIGS. 6D and 6E, as screw (210) is advanced further into aperture (120) at angle (b), head (240) of first screw (210) may apply force to the first angled ramp (152) and/or second angled ramp (154), causing orthopedic plate (110) to traverse in a direction (x). First screw (210) may be advanced into aperture (120) until head (240) of first screw (210) is inserted into second semicircular portion (160) of aperture (120), as shown in FIGS. 6F and 6G.

One or more threads (340) on head (240) of first screw (210) may be configured to mate with and/or lock to one or more threads (162) on the interior surface of second semicircular portion (160) of aperture (120). Additionally or alternatively, the one or more threads (340) on head (240) may be configured to cut into the interior surface of second semicircular portion (160) of aperture (120).

Figure 7:
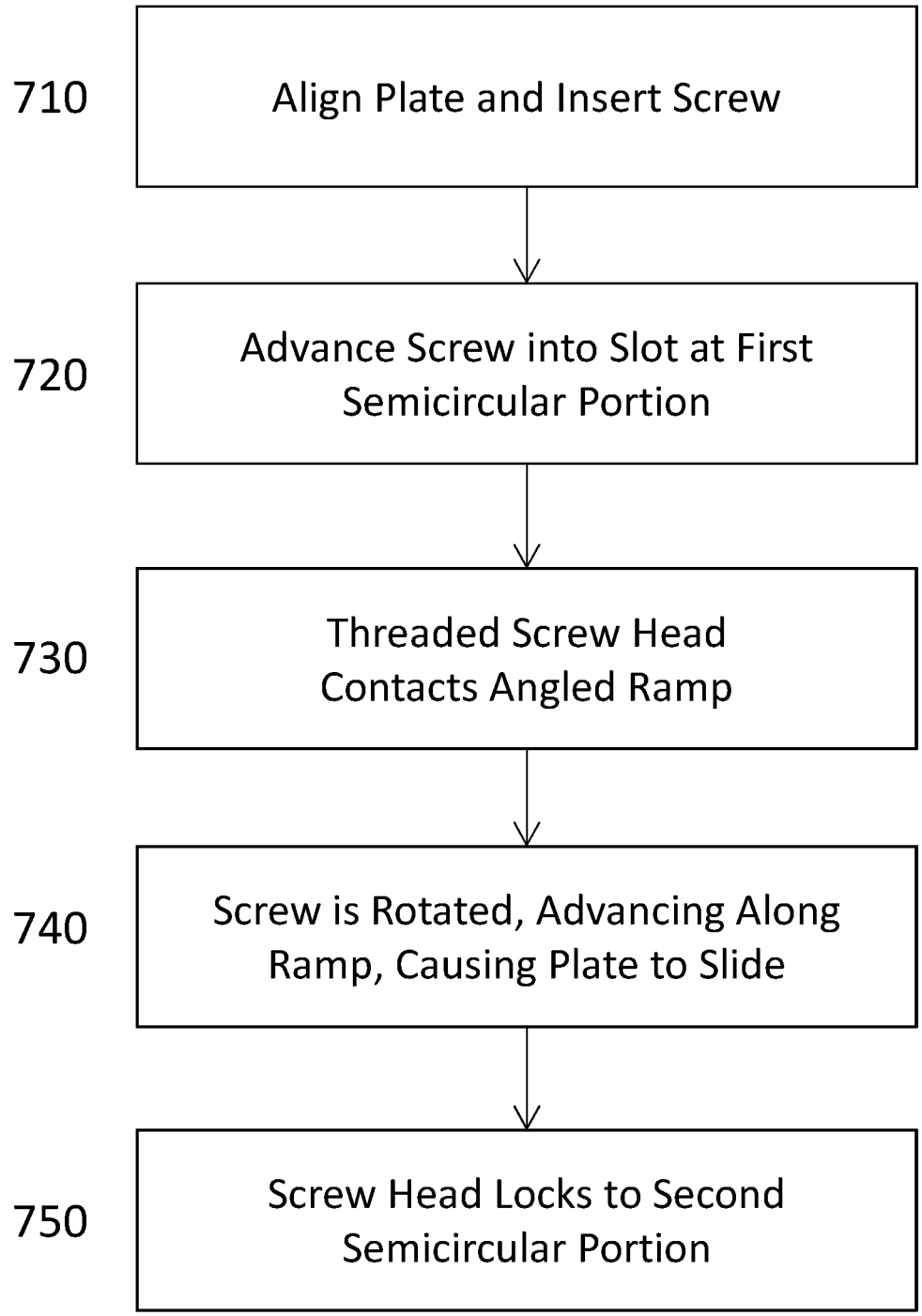
FIG. 7 is a flowchart depicting a method in accordance with the present invention.

FIG. 7 is a flowchart depicting a method of using the present invention. At Step 710, an orthopedic plate (110) having one or more apertures (119, 120, 121) as described above is aligned with a first bone (40) and a second bone (50). Preferably orthopedic plate (120) is joined to the second bone by, for example, inserting a screw into an aperture (121) and into the second bone. At Step 720, a screw (210) may be inserted into an aperture (120) comprising a slot as described above. Screw (210) may be inserted into a first semicircular portion (130) of aperture (120) at an angle between perpendicular and up to approximately 15 degrees from perpendicular to the top surface of orthopedic plate (110). At Step 730, the screw (210) is advanced into aperture (120) until a head (240) of screw (210) contacts one or more angled ramp (152, 154) in aperture (120). At Step 740, as the screw is rotated and advances further into aperture (120) and first bone (40), head (240) imparts downward force to the one or more angled ramps (152, 154), forcing the orthopedic plate to traverse to slide along the outer surface of first bone (40). At Step 750, the orthopedic plate advances relative to first screw (210) until head (240) of first screw (210) enters a second semicircular portion (160) of aperture (120). One or more threads on head (240) may be configured to lock to one or more threads and/or the interior surface of second semicircular portion (160). First screw (210) may lock to aperture (120) at the angle at which the screw was inserted into aperture (120) at Step 720.

While the invention has been described in detail with reference to embodiments for the purposes of making a complete disclosure of the invention, such embodiments are merely exemplary and are not intended to be limiting or represent an exhaustive enumeration of all aspects of the invention. It will be apparent to those of ordinary skill in the art that numerous changes may be made in such details, and the invention is capable of being embodied in other forms, without departing from the spirit, essential characteristics, and principles of the invention. Also, the benefits, advantages, solutions to problems, and any elements that may allow or facilitate any benefit, advantage, or solution are not to be construed as critical, required, or essential to the invention. The scope of the invention is to be limited only by the appended claims.

What is claimed is:

1. A system capable of fixating a first bone and a second bone, comprising:
   a first screw extending along a first longitudinal axis from a first end to a second end, said screw comprising a head at the first end and a shaft extending from the head to the second end, wherein the head extends from a top end to a bottom end, and the head has an outer surface comprising a thread;
   a second screw; and
   an orthopedic plate having a top surface, a bottom surface, a first aperture, and a second aperture, wherein the first aperture is a first slot extending along a second longitudinal axis from a first to a second end;
   wherein the first slot comprises a rectangular portion extending lengthwise from a first end to a second end along the second longitudinal axis, a first semicircular portion extending from the first end of the rectangular portion, and a second semicircular portion extending from the second end of the rectangular portion;
   wherein the diameter of the first semicircular portion and the diameter of the second semicircular portion are substantially the same as the width of the rectangular portion measured perpendicular to the second longitudinal axis, and the first semicircular portion and the second semicircular portion do not intersect;
   wherein the second semicircular portion comprises an interior surface and said interior surface is threaded, the second semicircular portion comprising a taper between the top surface and the thread;
   wherein the rectangular portion comprises two sides comprising interior surfaces that face each other, wherein an interior surface of at least one of the two sides comprises an angled ramp extending from the taper;
   wherein the orthopedic plate is configured to be secured to the second bone by inserting the second screw into the second aperture and into the second bone; wherein when the first screw is inserted into the first slot and into the first bone, rotating the first screw compresses the first bone and the second bone; and
   wherein the thread on the head of the first screw is configured to lock to the thread on the interior surface of the second semicircular portion when the screw is inserted at an angled orientation between perpendicular to the top surface of the plate and 15 degrees from perpendicular to the top surface of the plate.

2. The system of claim 1, wherein the head of the first screw has a truncated conical shape.

3. The system of claim 2, wherein the outer surface of the head of the first screw forms an angle to the first longitudinal axis that is approximately 15 degrees.

4. The system of claim 1, wherein the second semicircular portion of the first slot comprises a chamfered edge.

5. The system of claim 1, wherein the orthopedic plate comprises a second slot comprising a rectangular portion extending lengthwise from a first end to a second end along a third longitudinal axis, a first semicircular portion adjacent to the first end of the rectangular portion, and a second semicircular portion adjacent to the second end of the rectangular portion.

6. The system of claim 5, wherein the diameter of the first semicircular portion of the second slot and the diameter of the second semicircular portion of the second slot are substantially the same as the width of the rectangular portion of the second slot, measured perpendicular to the third longitudinal axis.

7. The system of claim 6, wherein the first semicircular portion of the second slot and the second semicircular portion of the second slot do not intersect.

8. The system of claim 7, wherein the first semicircular portion of the second slot has an interior surface and said interior surface is threaded.

9. The system of claim 8, wherein the rectangular portion of the second slot has an interior surface and the interior surface of the rectangular portion comprises an angled ramp.

10. The system of claim 5, wherein the head of the first screw has a truncated conical shape.

11. The system of claim 10, wherein the outer surface of the head of the first screw forms an angle to the first longitudinal axis that is approximately 15 degrees.

12. The system of claim 5, wherein the second semicircular portion of the second slot comprises a chamfered edge.

13. The system of claim 1, wherein the thread on the head of the first screw extends from the top end to the bottom end of the head.

* * * * *